United States Patent [19]

Ahrens

[11] 4,342,651
[45] Aug. 3, 1982

[54] PROCESS AND APPARATUS FOR PRODUCING STERILIZED AND BACTERIA-FREE WATER

[75] Inventor: Ulrich E. Ahrens, Springe, Fed. Rep. of Germany

[73] Assignee: Blutspendedientst der Landesverbande des Deutshen Roten Kreuzes Niedersachsen Oldenburg and Remen, GmbH, Hanover, Fed. Rep. of Germany

[21] Appl. No.: 130,390

[22] Filed: Mar. 14, 1980

Related U.S. Application Data

[63] Continuation-in-part of Ser. No. 934,350, Aug. 17, 1978, abandoned.

[30] Foreign Application Priority Data

Sep. 1, 1977 [DE] Fed. Rep. of Germany ....... 2739335

[51] Int. Cl.³ .................... B01D 31/00; B01D 13/00
[52] U.S. Cl. .................................... 210/636; 210/97; 210/254; 210/321.1; 422/28; 422/36
[58] Field of Search ............... 210/259, 636, 409, 637, 210/321.1, 321.2, 321.3, 97; 422/28, 36, 255, 241

[56] References Cited

U.S. PATENT DOCUMENTS

T912,007  1/1973  Rosenblatt ..................... 210/637
3,639,231  2/1972  Breszer ........................... 210/259 X
3,849,305  11/1974  Mahjikian ....................... 210/409
4,072,610  2/1978  Gow et al. ...................... 210/259 X
4,160,727  7/1979  Harris, Jr. ....................... 210/259 X
4,166,031  8/1979  Hardy ............................. 210/636 X

FOREIGN PATENT DOCUMENTS 2207868  6/1974  France ............................ 210/23 H

OTHER PUBLICATIONS

Vigo et al., Preparation of - - - Hyperfiltration," from J. Applied Polymer Science, vol. 21, 1977, pp. 3269-3290.
Goodall et al., "Process Water - - - Economicas," from Filtration & Separation, Nov./Dec. 1977, pp. 649-655.
Marquardt et al., "Modern - - - Unkehrosmose Anlgen," Hager & Elsasser GmbH, Stuttgart, Heft, 4/76.

Primary Examiner—Frank A. Spear, Jr.

[57] ABSTRACT

In a process and apparatus for obtaining sterilized and bacteria-free water suitable for medicinal injections and other purposes, deionized water is supplied to a reverse osmosis filter, which is impervious to attack by bacteria and which is arranged such that its entire surface may be sterilized, to obtain a sterile permeate and a portion of the deionized water supplied to the filter is recycled. The recycled portion of deionized water may be recycled through the deionization plant from which it is derived or through a closed circuit and may be recycled in combination with the sterile permeate.

19 Claims, 4 Drawing Figures

PROCESS AND APPARATUS FOR PRODUCING STERILIZED AND BACTERIA-FREE WATER

RELATED APPLICATION

This application is a continuation-in-part of my copending application Ser. No. 934,350, filed Aug. 17, 1978, now abandoned.

FIELD OF THE INVENTION

This invention relates to a process and apparatus for obtaining highly pure, sterilized, particle, pyrogen and germ-free water for medicinal injection preparations and other technical purposes, using completely salt-free or deionized water and a reverse osmosis filter.

BACKGROUND & SUMMARY OF THE INVENTION

For the production of sterilized, bacteria-free and apyrogenic water, such as is required for injection and infusion solutions, it has been proposed that the so-called reverse osmosis or hyperfiltration may be used.

Reverse osmosis using semipermeable membranes has been employed in which water of low salt content is separated from a salt-containing water. If such a membrane is subjected to a salt containing water under a pressure exceeding the osmotic pressure of the solution, water of low salt content passes through and germs or bacteria and pyrogens are also retained by the membrane.

Reverse osmosis can be used to remove germs, bacteria and pyrogens from water which has previously been deionized by any conventional means.

Membranes which have been used for this purpose have been formed of acetyl celluloses, polyamides or polyolefins. Water transportation through the membranes is impeded by the concentration or polarization that occurs of retained substances. By a suitable excess flow oriented tangentially to the surface, such concentration and polarization can be reduced and the membrane surface can be largely kept clear of microscopic and larger bodies such as germs, bacteria and pyrogens.

The disadvantage of the known processes and apparatus comprising the semipermeable membranes is, however, that the membranes must be continually subjected to the action of water, in order that the semipermeable membranes are not damaged by bacteria which are unable to pass through the membranes. If the installation is shut down and no water flow takes place over the membrane, colonies of bacteria can form which attack the membrane, so that when operation is resumed germs will pass through the fairly large holes which are now present. On the other hand, a requirement for such pure water usually does not exist continuously, or the requirement for pure water is highly fluctuating, so that a solution must be found for collecting and storing the sterile permeate under sterile conditions.

Storage of the sterile permeate has normally been done in containers maintained under sterile conditions with the permeate in the containers at an elevated temperature, preferably 85° C., while it is stored. Such storage is not particularly economical. The provision of storage vessels for the sterilized permeate incurs capital costs and also the vessels occupy valuable space. Additionally, the vessels must be kept sterile. The energy consumption is considerable both for heating and maintaining the temperature at 85° C. and also for cooling the permeate when required for the intended purposes.

A further disadvantage is that, due to the particular nature of the above-described process of reverse osmosis, a considerable proportion of the water supplied to the semipermeable membrane serves only as excess water for maintaining at the surface of the membrane a flow of water for the above-mentioned reasons.

Systems in which a portion of the deionized water which is supplied to the reverse osmosis filter or membrane has been recycled to maintain the membrane as free as possible of bacteria and pyrogens which have been retained on the filter to minimize the possibility of bacteria attack on the filter are disclosed, for example, in French Pat. No. 2,207,868 and Marquardt, K., *Moderne Wasseraufbereitung in zentralen Dialysestationen durch Umkehrosmose-Anlagen,* Hager and Elsasser GmbH, Stuttgart, Heft 4/76. In addition, the latter cited German publication also discloses a system in which sterile permeate may be recycled to eliminate the need for storage vessels and their attendant disadvantages during periods of low sterile permeate demand.

Although the last mentioned systems have solved some of the problems which exist in the removal of bacteria using reverse osmosis filters or membranes, they have not successfully solved all of the problems that must be overcome in order for such membrane systems to be fully accepted for the preparation of water which is of sufficient purity for use in the injection of medicinals into the human body. Although such reverse osmosis filters or membranes have been accepted by the United States Pharmacopoeia for the preparation of pyrogen-free water for injection, they have not been accepted for the preparation of bacteria-free water for this purpose. Goodall, J., *Process Water Purification; RO Techniques and Economics,* Proceedings of the Filtration Society, 1977, p. 652.

The present inventor has discovered that even though recycling of a portion of the deionized water removes substantial amounts of bacteria from the filter surfaces and reduces the likelihood of attack on the membrane, some bacteria still remains which will attack the membrane and eventually a certain amount of bacteria will enter the permeate at these points of attack. Moreover, in the prior systems it has been generally necessary to recycle a substantial amount of the deionized water to insure that a sufficient flushing action occurs at the membrane surface to delay for as long as possible attack of the membrane by the bacteria. Such substantial recycling of the deionized water is not only wasteful of pumping energy, but also results in reduced system capacity and increased cooling requirements to cool the recycled water which is heated by the pumping energy necessitated by such recycling.

The inventor has also discovered that where sterilizing fluids have been periodically employed to flush the prior systems, that the membranes of these systems were not of sufficient configuration to enable the sterilant to reach all portions of the membrane surfaces. Thus, the membranes were subjected to attack by bacteria on those portions of their surfaces which could not be reached by the sterilizing fluid and bacteria escaped into the permeate.

The process and apparatus incorporating the principles of the present invention is capable of producing a consistently sterile, bacteria and pyrogen-free permeate suitable for medicinal injections and other purposes contrary to the aforementioned Goodall publication and overcome all of the aforementioned disadvantages of the prior systems. The process and apparatus incorporating the principles of the present invention achieves this result while at the same time minimizing energy and capital requirements and maximizing capacity.

In one principal aspect of the present invention, a process for producing sterilized water free of bacteria and pyrogens and suitable for medicinal injection includes the step of circulating deionized water into contact with a reverse osmosis-filter formed of a material which is substantially impervious to attack by bacteria in the water. A portion of the deionized water is passed through the filter to obtain a sterile permeate and another portion is recycled from the filter. The sterile permeate which is not used is also recycled to the filter. At least periodically all portions of the surface of the filter are sterilized with a sterilizing fluid.

In another principal aspect of the present invention, apparatus for producing sterilized water free of bacteria and pyrogens and suitable for medicinal injection comprises a source of deionized water, a reverse osmosis filter formed of a material which is substantially impervious to attack by bacteria in the water, means for supplying the deionized water from the source to and into contact with the filter and passing a portion of the deionized water through the filter to obtain a sterile permeate. The apparatus also includes means for recycling another portion of the water which is not passed through the filter from the filter and means removes the sterile permeate from the filter withdraws the permeate for use and recycles the remainder of the permeate to the filter. Means at least periodically supplies a sterilizing fluid to the filter and the filter is constructed and arranged such that all portions of its surface are exposed to the sterilizing fluid.

In another principal aspect of the present invention, the filter which is impervious to bacteria attack is formed of a fluorine substituted polymer.

In still another principal aspect of the present invention, the filter is arranged in coil or plate form to enable the sterilizing fluid to reach all portions of the surface thereof.

These and other objects, features and advantages of the present invention will become apparent when considering the following detailed description of a preferred embodiment.

DESCRIPTION OF THE PREFERRED EMBODIMENT

Figure 1:
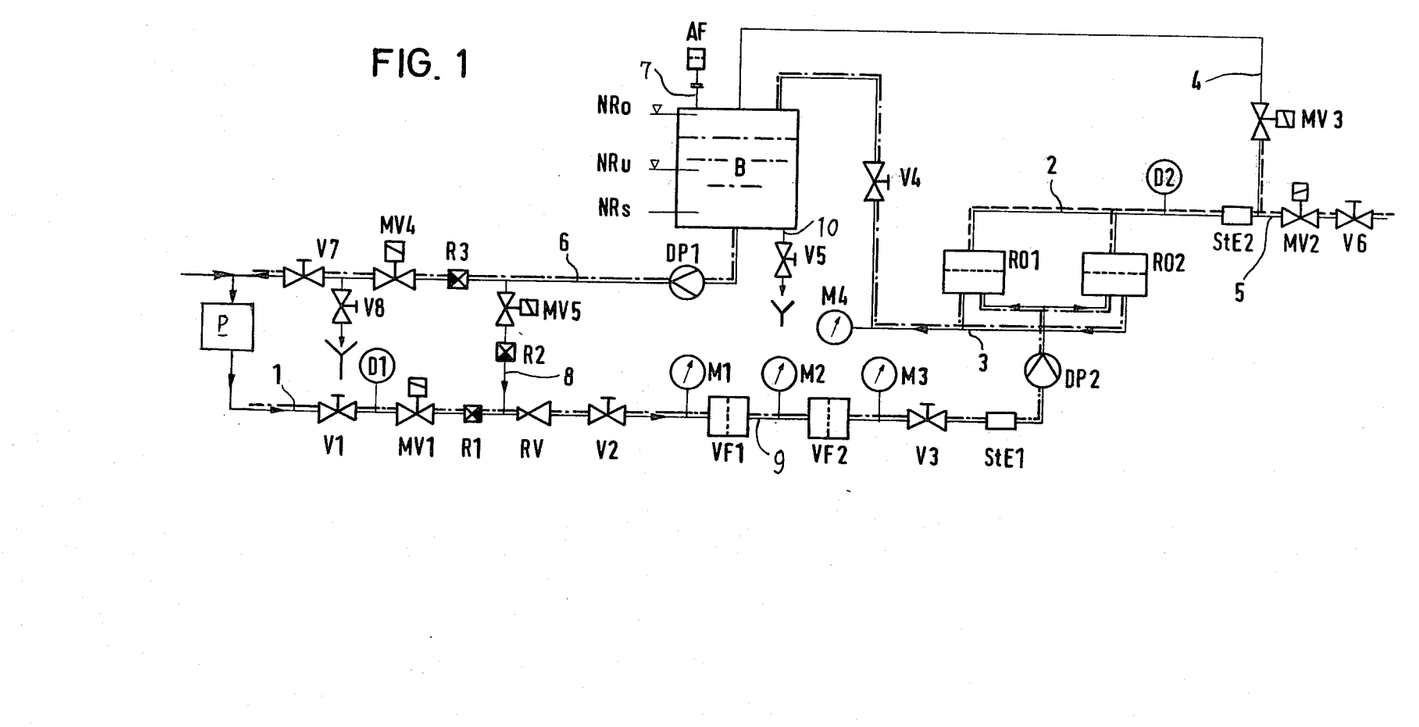
FIG. 1 is a schematic diagram illustrating the operation of the preferred embodiment of the invention for obtaining pure water, the path of the supplied deionized water being shown in chain-dotted lines and the path of the permeate in dotted lines.
Figure 2:
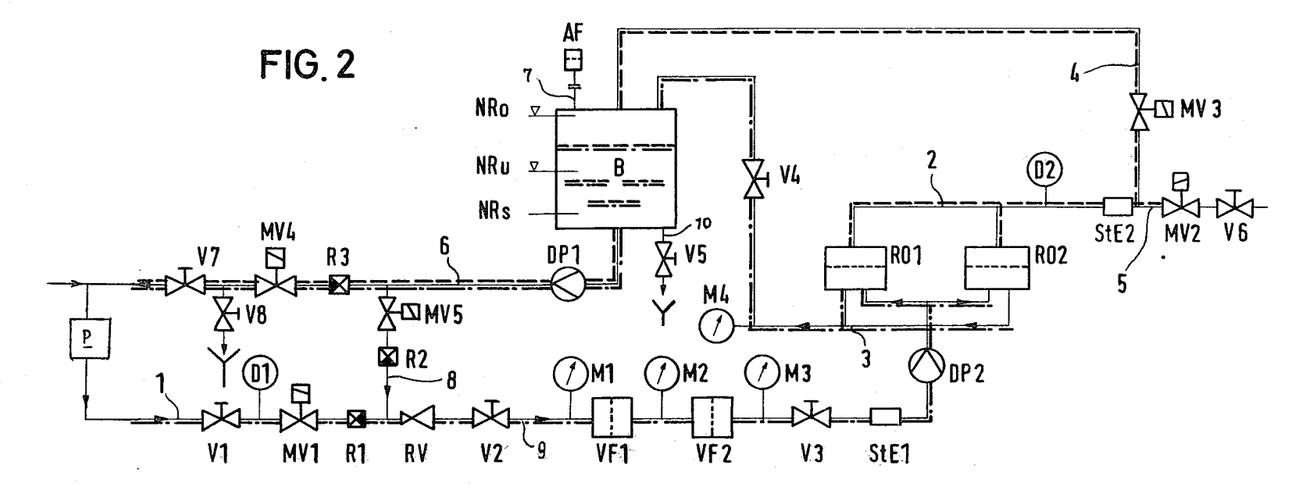
FIG. 2 is a view similar to FIG. 1 and illustrates the operation when no permeate is being removed, but deionized water is being supplied from a deionization plant.

In FIGS. 1 and 2, deionized water which is derived from a deionization plant P and which is to be treated is supplied along an inlet line 1 and flows in the direction of the arrow through a shut-off valve V1, a solenoid valve MV1 and a non-return valve R1 into a supply line 9 which includes a pressure-reducing valve RV, a further shut-off valve V2 and a first prefilter VF1. The water leaving the prefilter VF1 flows into a second prefilter VF2, through a shut-off valve V3 and finally through a sampling station StE1 to a pump DP2 which generates the pressure necessary for operating the reverse osmosis filters RO1 and RO2, the pressure being between 10 and 80 bars according to the type of filter.

Only a portion of the deionized water supplied passes as permeate through the reverse osmosis filters and a discharge line 2 and an outlet line 5 incorporating valves MV2 and V6. A further sterile sampling station StE2 is contained in the discharge line 2.

The balance of the supplied deionized water flows through line 3 and a valve V4 into a compensating vessel B and fills this vessel until the upper level mark NRo of the level regulator is reached. The vessel B has an outlet communicating with a return line 6 which includes a pump DP1 which is switched on by the level regulator NRo when a predetermined liquid level is reached so that liquid is returned along line 6 into the deionization plant P until the level NRu is reached in the vessel B. This return flow along line 6 passes through a non-return valve R3, a solenoid valve MV4 and a shut-off valve V7. Between the solenoid valve MV4 and the shut-off valve V7 an emptying line containing a shut-off valve V8 is incorporated as a branch. Before, between, and after the prefilters VF1 and VF2, manometers M1 to M3 are preferably disposed as illustrated.

In the operation of the circuit shown in FIG. 1, permeate is drawn off along outlet line 5 for use and a portion of the supplied deionized water is recycled along return line 6 to the deionization plant P.

In FIG. 2, the circuit arrangement is shown when no permeate is drawn from the outlet line 5, but the deionization plant P is still in operation. In order to avoid the expense initially described of storage tanks and keeping them at a temperature of 85° C., a recycle line 4 connects the discharge line 2 to the compensating vessel B and is branched off between the sterile sampling station StE2 and the valve MV2, just upstream of the latter. In this recycle line, a solenoid valve MV3 is disposed, which is open when no permeate is drawn off, but is closed when permeate is drawn off. It should be mentioned here that this recycle line for the permeate branches off very close to and upstream of the valve MV2, in order that stationary water between the branch and the solenoid valve MV2 shall be avoided and the maximum volume of the plant shall be in the flowing state, so that growth of germs and bacteria is not favoured.

It will be appreciated that FIG. 2 illustrates the operating state in which no permeate is being withdrawn and the permeate together with a proportion of the supplied deionized water is supplied to the deionization plant P which is supplying the deionized water.

Figure 3:
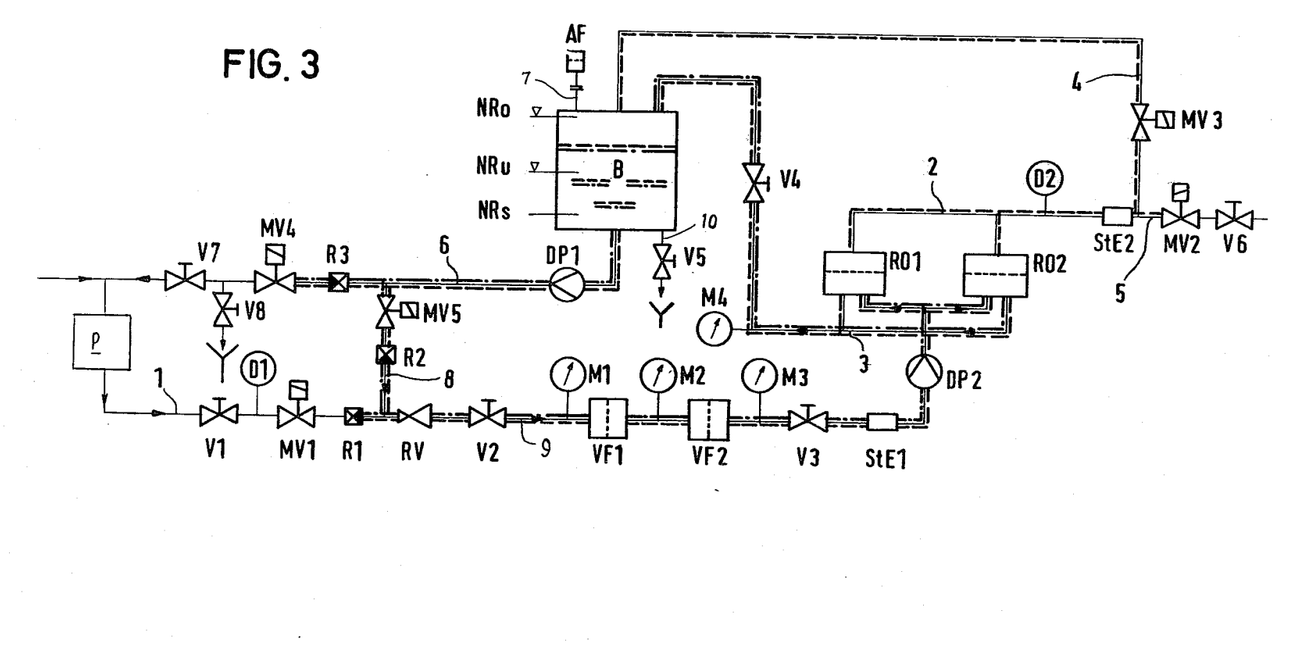
FIG. 3 is a view similar to FIG. 2 and illustrates the operation when no deionized water is supplied from the plant.

In the condition illustrated in FIG. 3, no deionized water is derived from or returned to the deionization plant P. A short-circuit line 8 incorporating a normally closed solenoid valve MV5 and a non-return valve R2 connects the return line 6 to the supply line 1 from a position upstream of the non-return valve R3 to a position between the valves R1 and RV. In this case, the pressure PD1 sensed by the pressure monitor D1 is smaller than a predetermined critical pressure PD1 crit., and this operates to close valves MV1 and MV4 and open valve MV5. Also, MV2 is closed or held closed and MV3 is opened or held open. In addition, in order to prevent harmful heating up of the plant, the pump DP2 is switched off.

The pump DP1 maintains a weak circulation through the entire plant, as can be seen from the switching diagram below of the plant. In this condition of the circuit, the supplied deionized water and the permeate are circulated in a closed circuit or loop.

As can be seen from FIG. 3, the compensating vessel B is equipped with a connecting line 7, through which a sterilizing disinfecting agent, for example a 2% formalin solution, can be periodically introduced. This formalin solution, when supplied, flows out of the vessel B through the pump DP1, along the line 8 into the line 9 leading to the prefilters, through the pump DP2, and then partially as an excess portion back into the compensating vessel B, and also through the reverse osmosis filters RO1 and RO2, through the lines 2 and 4 back into the compensating vessel B, because the solenoid valve MV3 is opened, but the solenoid valve MV2 is closed.

In the line 7, a breathing filter AF is provided, through which a sterile ventilation of the compensating vessel B can be carried out.

It can be seen that when the pumps DP1 and DP2 are operating, a complete sterilization of the circuit of the plant and a wide-ranging sterilization of the entire plant by means of the formalin solution introduced through the line 7 is possible. There remain only short lengths of pipe and some valves in the supply line 1 for the fully deionized water and in the return line 6 leading back to the deionization plant P, as components which are not swept by this formalin solution. This defect can, however, be overcome at the lines near to the circuit, by causing these remaining portions to be traversed by the formalin solution when the plant is flushed through and by so arranging the line 8, which short-circuits the lines 9 and 6, that the proportion of non-sterilized pipe components and valves is kept as small as possible.

Figure 4:
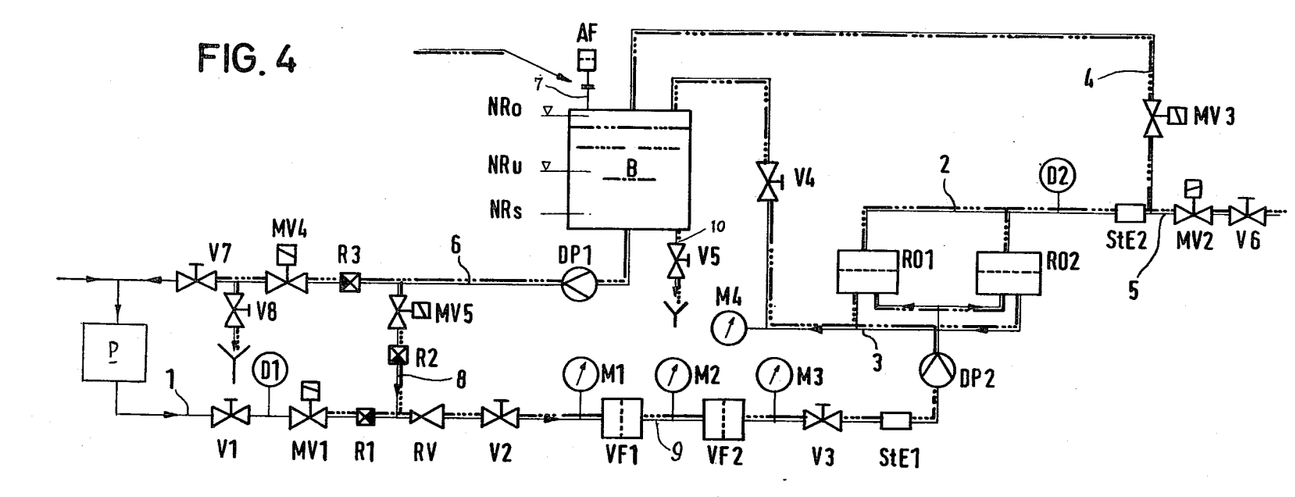
FIG. 4 is a view similar to FIG. 3 and illustrates the operation when the circuit is being sterilized.

The change-over from the operating state according to FIGS. 1 and 2 into the operating state with its function according to FIG. 4 can be carried out in practice automatically either after the elapse of specific periods or after specific quantities have flowed through. When changing over from the state according to FIG. 1 or 2 into the state according to FIG. 4, the valves MV1, MV2 and MV4 would be closed and a disinfecting agent introduced into the compensating vessel through the line 7, optionally together with water as a diluting agent. The water contained in the plant can be entirely or partially discharged from the vessel B through a line 10 after opening a valve V5 in the line 10. The arrangement and layout should take account of this accordingly.

In the switching diagram given below, the four methods of operation of the plant are illustrated in a summary manner by indicating the position of the valves and the operating of the pumps. In this switching diagram, the terms are also explained and the references used in FIGS. 1 and 4 are summarized.

It has already been pointed out that an increase in temperature results from the circulation of the excess water and non-removed highly pure water or permeate. For this reason, the compensating vessel B or another location of the circuit may be equipped with a thermo-probe which measures the temperature of the water in the circuit and switches appropriate electric circuits which, by switching off pumps or switching on cooling means, leads to a reduction in the temperature of the water in the circuit.

In operating methods 3 and 4, a closed circuit exists through the short-circuit line 8. In such a case, water could escape continuously from the plant through a defect in any portion of it. In order to prevent consequent damage to the plant, and especially to the reverse osmosis filters, the level controller in the compensating vessel B can be equipped with a contact such as NRs for switching off the pressure pump DP1 and triggering an alarm.

Explanation of Abbreviations of Flow Diagram and Description of Functioning

PD1 crit.: critical pressure, which is smaller than the lowest full deionization water pressure with the deionization plant P in operation. Objective: switching over from operating method 1 or 2 to 3, when the deionization plant P goes out of operation or other pressure failure takes place upstream of D1.
PD2 crit.: critical pressure
For Operating Method 1: smaller than a maximum pressure of PD2
For Operating Method 2: smaller than the pressure set at pressure reducing valve RV
For Operating Method 3: smaller than the pressure set at pressure reducing valve RV
For Operating Method 4: as for operating method 1
Pu: excess flow pressure adjustable
o: valve opened
⊙: valve closed
AF: breathing filter
VE: fully desalinated water
V: hand valve
MV: solenoid valve
RV: pressure reducing valve
VF: prefilter
StE: sterile sampling
DP: Pressure pump
RO: reverse osmosis plant
R: non-return valve
M: manometer
D: pressure switch
B: reject vessel
NR: level controller
NRo: level controller top
NRu: level controller bottom
NRs: level controller safety In a specific embodiment of the plant for carrying out the process according to this invention, the two reverse osmosis filters RO1 and RO2, the pump DP2 and the return flow throttle valve V4 should be adapted to one another and may be designed, for example, for a permeation rate per hour of 80 l. The pump then produces a pressure of, for instance, 14 bars.

| SWITCHING DIAGRAM FOR PLANT FOR OBTAINING STERILE AQUA PRO INJECTIONS |
| --- |

| Method of functioning | V1 | D1 | MV1 | V2 | V3 | DP2 | V4 | D2 | MV2 | V6 | MV3 | NR | AF | V5 | DP1 | MV4 | V7 | V8 | MV5 |
| --- | --- | --- | --- | --- | --- | --- | --- | --- | --- | --- | --- | --- | --- | --- | --- | --- | --- | --- | --- |
| 1 Draw-off of sterile aqua pro injections full deionisation in operation | o | PD1 > PD1 crit. | o | o | o | on | PU | PD2 < PD2 crit. | o | o | • | top bottom | connected | • | on off | o | o | • | • |
| 2 No draw-off of sterile aqua pro injections; full deionisation plant in operation | o | PD1 > PD1 crit. | o | o | o | on | PU | PD2 < PD2 crit. | • | o | o | top bottom | connected | • | on off | o | o | • | • |
| 3 Full deionisation plant not in operation | o | PD1 ≦ PD1 crit. | • | o | o | off | PU | PD2 < PD2 crit. | • | o | o | top bottom safety | connected | • | on off | • | o | • | o |
| 4 Chemical sterilisation of plant with formalin | • | PD1 ≦ > PD1 crit. | • | o | o | on off | PU | PD2 < PD2 crit. | • / o | o | o / • | top bottom safety | not connected | • / o | on off | • / o | • | • / o | o / • |

The volume of the compensating vessel B is then, for example 100 l and the total volume of the plant will be 120 l, depending upon the length of the lines 2 and 4. The pump DP1 is designed according to the characteristics of the reverse osmosis filters and the flocking characteristic of the pump DP2, that is the characteristic when this pump is shut down.

The process and apparatus of the present invention offers a system in which the recycling of a portion of the dionized water with or without the permeate impairs colonies of bacteria forming at the membrane of the reverse osmosis filter even under circumstances where there is no demand for the permeate. However, as previously mentioned, it has been found that such recycling of deionized water is not sufficient to prevent eventual attack of the membrane by colonies of bacteria. In the present invention, it has been discovered that this attack can be prevented by two additional features. One feature is to employ a membrane material which is substantially impervious to bacteria attack so that even if some bacterial growth is experienced on the membrane, the membrane will remain intact. The other feature is to employ a membrane construction and arrangement which can be contacted over its entire surface by the sterilizing disinfecting agent during the sterilizing portion of the cycle of operation.

It has been found that a reverse osmosis filter or membrane formed of a halogenated polymer is substantially impervious to bacteria attack. A preferred membrane material for this purpose, and to which bacteria do not easily attach, is a fluorine substituted polymer. Such membrane sheets may be formed as described in 21 Journal of Applied Polymer Science, 1977, pp. 3269-3290.

Some examples of membrane materials which are suitable for use in the present invention include homo- and copolymers of polytetrafluoroethylene and polytrifluorochroroethylene. One suitable example of polytetrafluoroethylene may have the following properties:

| | |
| --- | --- |
| Density: | 2.0 to 2.3 |
| Temperature Resistance: | −100° to +260° C. |
| Load Carrying Capacity According to Vicat VDE-Norm 0302 (German Standard): | 110° C. |
| Heat Loading Capacity or Heat Distortional Temperature (according to ASTM D 648) | |
| At 166 PSI: | 130° to 190° C. |
| At 264 PSI: | 50° to 60° C. |
| Refractory Index: (according to German Standard DIN (53491) | 1.35 | and a suitable example of polytrifluorochloroethylene may have the following properties:

| | |
| --- | --- |
| Density: | 2.0 to 2.1 |
| Melting Point | about 212° C. |
| Load Carrying Capacity according to Vicat VDE-Norm 0302 (German Standard): | 76° to 89° C. |
| According to Martens DIN 53458: | 56° to 64° C. |
| Heat Distortional Temperature at 264 PSI: | 50° to 58° C. |
| Temperature Resistance: | Between +150° and −40° C. |
| Refractory Index: | 1.425 |
| Thickness of Foil: | Between 50 and 100 microns |

Copolymers of polytetrafluoroethylene and hexafluoropropylene are also suitable.

Suitable polytetrafluoroethylene material as outlined above is available from the William Gore Company, Elkton, Maryland.

Some polyamide materials are also sufficiently impervious to bacteria attack that they are useful in the present invention. Such suitable polyamide materials include wound filters of this material which are available from Forschungsinstitut Berghof GmbH., Teubingen, West Germany and tubes of this material which are available from Kalle, Wiesbaden, West Germany.

It has also been discovered that current reverse osmosis membranes of the hollow fiber type are not suitable for the production of the bacteria-free permeate desired by the present invention. Current hollow fiber membranes cannot be completely sterilized by the sterilizing disinfecting agent because such agent cannot reach all of the surfaces of the membrane. It has been found, however, that membranes arranged either in flat sheets or plates or in spiral or coil form can be easily and completely sterilized because the sterilizing disinfecting agent can reach all of the surfaces of the membrane during the sterilizing portion of the cycle. Thus, the latter mentioned membrane arrangements are preferred. Suitable flat sheet and spiral or coil osmosis cell apparatus is available from the firms Satorius, GmbH, Goettingen, Germany and Deutsche Millipore GmbH, Neuisenburg, Germany.

Due to the fact that in the present invention, recycling of a portion of the deionized water which contacts the membrane is not the sole feature relied upon to prevent bacteria attack and damage to the filter, the amount of recycled deionized water can be reduced and the amount of such water which passes through the membrane can be increased to increase the amount of sterile permeate produced by the invention. It has been found that as much as 70-90% of the deionized water can be passed through the membrane and still result in the consistent production of highly sterile, bacteria and pyrogen free permeate which is suitable for medicinal injection purposes. This is particularly true where the deionized water is caused to turbulently contact the inlet side of the membrane by well known techniques. By minimizing the amount of recycled deionized water and maximizing the flow through the membrane, energy consumption and capital requirements of the process and apparatus are minimized and capacity is maximized.

It will be understood that if cooling is to be carried out due to lengthy recycling of either or both the deionized water or sterile permeate, it may be accomplished, for example, by recycling the water to a point upstream of the deionization plant. If other facilities for the cooling of the circuit water are present in the region where this plant is used, then these can of course be utilized.

The circuit arrangement of the excess portion of the deionized water conducted to the reverse osmosis and also the parallel circuit for the permeate include as much as possible of the equipment necessary for carrying out the process, in order that dead spaces shall be avoided and germs shall not be capable of collecting anywhere. The equipment is composed of components and materials of known types, and also the valves are of known construction. Non-rusting steel, glass or quartz glass are preferably used as the materials.

It will also be understood that a compensating vessel of the smallest practicable capacity with a level controller is contained in the circuit of the excess portion of the water to compensate for fluctuation in volume.

Although a preferred embodiment of the invention has been described in detail, the invention is not to be limited to only such embodiment, but rather only by the appended claims.

What is claimed is:

1. A process for producing sterilized water free of bacteria and pyrogens and suitable for medicinal injection comprising the steps of:
   circulating deionized water to be sterilized into contact with a reverse osmosis non-hollow, non-fibrous filter formed of a material which is substantially impervious to attack by bacteria in the water,
   passing a portion of said deionized water through said filter to obtain a sterile permeate,
   recycling another portion of said deionized water from said filter,
   recycling the sterile permeate which is not used to said filter, and
   at least periodically sterilizing all portions of the surface of said filter with a sterilizing fluid.

2. A process according to claim 1 in which the deionized water is derived from a deionization plant.

3. A process according to claim 1 in which the recycled sterile permeate is combined with said recycled portion of the deionized water.

4. A process according to claim 3 in which the said recycled sterile permeate is combined with said recycled portion of the deionized water in a compensating vessel.

5. A process according to claim 1 in which said filter is formed of a halogen substituted polymer.

6. A process according to claim 5 in which said halogen is fluorine.

7. A process according to claim 5 in which said halogen substituted polymer is polytetrafluroethylene.

8. The process according to claim 1 wherein said filter is arranged in coil or plate form to enable said sterilizing fluid to reach all portions of the surface thereof.

9. A process according to claim 1 in which the deionized water is derived from a deionization plant and said recycled permeate is combined with said recycled portion of the deionized water, in which said portion of said deionized water which is passed through said filter comprises 70-90% of the deionized water which is circulated into contact with said filter, in which said deionized water turbulently contacts said filter, and in which said filter is formed of a fluorine substituted polymer and is arranged in coil or plate form to enable said sterilizing fluid to reach all portions of the surface thereof.

10. A process according to claim 1 in which said portion of said deionized water which is passed through said filter comprises 70-90% of the water which is circulated into contact with said filter.

11. A process according to claim 1 in which said deionized water turbulently contacts said filter.

12. Apparatus for producing sterilized water free of bacteria and pyrogens and suitable for medicinal injection comprising:
   a source of deionized water,
   a reverse osmosis filter formed of a material which is substantially impervious to attack by bacteria in the water,
   means for supplying deionized water from said source to and into contact with said filter and passing a portion of said deionized water through said filter to obtain a sterile permeate,
   means for recycling another portion of said water which is not passed through said filter from said filter,
   means for removing said sterile permeate from said filter, said last mentioned means including means for withdrawing sterile permeate for use and recycling the remainder of said sterile permeate to said filter, means for at least periodically supplying a sterilizing fluid to said filter, said filter being constructed and arranged such that all portions of the surface of said filter are exposed to said sterilizing fluid, a compensating vessel, an outlet line for removing said sterile permeate for use, a recycle line connecting the sterile permeate side of said filter to said compensating vessel, a second recycle line connecting said means for supplying deionized water to said compensating vessel, a return line connecting said compensating vessel to said source, a short-circuit line connecting said return line to said means for supplying deionized water, first valve means in said outlet line selectively operable to open and close said outlet line, second valve means in said first mentioned recycle line selectively operable to close and open the first mentioned recycle line, and third valve means selectively operable to close and open said short-circuit line.

13. Apparatus according to claim 12 including fourth valve means in said means for supplying deionized water upstream of said connection to said short-circuit line and operable to open and close said means for supplying deionized water, and fifth valve means in said return line downstream of said connection to said short-circuit line and operable to open and close said return line.

14. Apparatus according to claim 12 including a pump in said return line upstream of said connection to said short-circuit line and a level controller associated with said compensating vessel and responsive to the liquid level therein to control said pump and maintain said liquid level below a predetermined value.

15. Apparatus according to claim 12 including a first liquid sampling station in said means for supplying deionized water and a second liquid sampling station in said outlet line.

16. Apparatus for producing sterilized water free of bacteria and pyrogens and suitable for medicinal injection comprising:

a source of deionized water, a reverse osmosis non-hollow, non-fibrous filter formed of a material which is substantially impervious to attack by bacteria in the water, means for supplying deionized water from said source to and into contact with said filter and passing a portion of said deionized water through said filter to obtain a sterile permeate, means for recycling another portion of said water which is not passed through said filter from said filter, means for removing said sterile permeate from said filter, said last mentioned means including means for withdrawing sterile permeate for use and recycling the remainder of said sterile permeate to said filter, means for at least periodically supplying a sterilizing fluid to said filter, all portions of the surface of said non-hollow, non-fibrous filter being exposed to said sterilizing fluid, a compensating vessel, an outlet line for removing said sterile permeate for use, a recycle line connecting the sterile permeate side of said filter to said compensating vessel, a second recycle line connecting said means for supplying deionized water to said compensating vessel, a return line connecting said compensating vessel to said source, a short-circuit line connecting said return line to said means for supplying deionized water, first valve means in said outlet line selectively operable to open and close said outlet line, second valve means in said first-mentioned recycle line selectively operable to close and open the first-mentioned recycle line, and third valve means selectively operable to close and open said short-circuit line.

17. Apparatus according to claim 16 including fourth valve means in said means for supplying deionized water upstream of said connection to said short-circuit line and operable to open and close said means for supplying deionized water, and fifth valve means in said return line downstream of said connection to said short-circuit line and operable to open and close said return line.

18. Apparatus according to claim 16 including a pump in said return line upstream of said connection to said short-circuit line and a level controller associated with said compensating vessel and responsive to the liquid level therein to control said pump and maintain said liquid level below a predetermined value.

19. Apparatus according to claim 16 including a first liquid sampling station in said means for supplying deionized water and a second liquid sampling station in said outlet line.

* * * * *

UNITED STATES PATENT AND TRADEMARK OFFICE
CERTIFICATE OF CORRECTION

PATENT NO. : 4,342,651
DATED : August 3, 1982
INVENTOR(S) : Ulrich E. Ahrens

It is certified that error appears in the above—identified patent and that said Letters Patent are hereby corrected as shown below:

On the cover page, item [73] delete Remen and insert --Bremen--.

On the cover page, item [73] delete Hanover and insert --Hannover--.

Signed and Sealed this

Twenty-sixth Day of October 1982

[SEAL]

Attest:

GERALD J. MOSSINGHOFF

Attesting Officer     Commissioner of Patents and Trademarks